United States Patent [19]

Ishikawa et al.

[11] Patent Number: 5,704,367
[45] Date of Patent: Jan. 6, 1998

[54] RESPIRATION MONITOR FOR MONITORING RESPIRATION BASED UPON AN IMAGE SIGNAL OF A FACIAL REGION

[75] Inventors: Norio Ishikawa; Hidehiro Hosaka; Ryoichi Ochiai, all of Tokyo, Japan

[73] Assignee: Nihon Kohden Corporation, Tokyo, Japan

[21] Appl. No.: 707,209

[22] Filed: Aug. 30, 1996

[51] Int. Cl.$^6$ ............................................. A61B 5/008
[52] U.S. Cl. .................................. 128/716; 128/664
[58] Field of Search ................ 128/664, 716–719, 128/721–724, 745, 922; 364/413.02, 413.03; 250/339.04; 382/110

[56] References Cited

U.S. PATENT DOCUMENTS

| | | | |
|---|---|---|---|
| 5,107,845 | 4/1992 | Guern | 128/664 |
| 5,309,921 | 5/1994 | Kisner et al. | 128/719 |
| 5,386,831 | 2/1995 | Gluck | 128/664 |
| 5,505,199 | 4/1996 | Kim | 128/716 |
| 5,570,698 | 11/1996 | Liang et al. | 128/745 |

*Primary Examiner*—Jennifer Bahr
*Assistant Examiner*—Bryan K. Yarnell

*Attorney, Agent, or Firm*—Sughrue,Mion,Zinn,Macpeak & Seas, PLLC

[57] ABSTRACT

A respiration monitor of the invention includes: an infrared camera for forming an image of a face; an operation section for selecting an imaging temperature to be set for the infrared camera out of a predetermined temperature range and setting the selected imaging temperature; an image memory for storing a facial image signal outputted from the infrared camera; a control section for defining a facial region in the facial image signal, binarizing the facial image signal within the facial region, calculating and outputting a respiratory waveform signal from a change in an area of the facial region every inspiration, and outputting an alarm by judging an apnea when a condition in which there is no change in the area of the facial region lasts for a predetermined time; an alarm section for generating an alarm out of the alarm signal; a synthesis section For synthesizing the facial image signal with the respiratory waveform signal; and a display apparatus for inputting the facial image signal and the respiratory waveform signal synthesized and outputted from the synthesis section, chronologically continuously displaying the facial image with the area of the facial region of the facial image changing, and displaying a respiratory waveform so as to correspond to the facial image with the area of the facial region of the facial image changing.

5 Claims, 3 Drawing Sheets

RESPIRATION MONITOR FOR MONITORING RESPIRATION BASED UPON AN IMAGE SIGNAL OF A FACIAL REGION

BACKGROUND OF THE INVENTION

1. Field of the Invention

The invention relates to a respiration monitor that detects, e.g., a respiratory condition of a patient in the form of an image.

2. Related Art

Methods such as an electrode impedance method and a thermistor method have heretofore been available for measuring respirations, and monitoring apneas in particular. The electrode impedance method is characterized as attaching electrodes to a body and measuring a voltage obtained from a change in impedance between the electrodes caused by a respiration. The thermistor method is characterized as attaching a sensor such as a thermistor to the vicinity of the nostrils of a patient and detecting a voltage corresponding to a change in resistance accompanied by a change in the temperature of the expired gas during respiration. These methods have been extensively employed since electrodes and thermistors are inexpensive and measurement of respiratory conditions is easy.

However, in respiration monitoring based on the electrode impedance method and the thermistor method, sensors such as electrodes and thermistors attached to ends of lead wires are set onto a body in a contact manner. Therefore, the setting of the electrodes and the sensors and the handling of the lead wires are cumbersome. In addition, it may, in some cases, be doubtful that an obtained respiratory waveform is genuine due to its being derived from a movement such as turning over in bed or a movement such as coughing which is not the respiration of the patient.

SUMMARY OF THE INVENTION

Therefore, in view of the aforementioned problems, the object of the invention is to provide a respiration monitor capable of reliably monitoring respiratory conditions of a patient in a noncontact and noninvasive manner.

A respiration monitor of the present invention includes: an infrared camera for forming an image of a face; an operation section for selecting an imaging temperature to be set for the infrared camera out of a predetermined temperature range and setting the selected imaging temperature; an image memory for storing a facial image signal output from the infrared camera; a control section for defining a facial region in the facial image signal, binarizing the facial image signal within the facial region, calculating and outputting a respiratory waveform signal from a change in an area of the facial region every inspiration, and outputting an alarm by judging an apnea when a condition in which there is no change in the area of the facial region lasts for a predetermined time; an alarm section for generating an alarm out of the alarm signal; a synthesis section for synthesizing the facial image signal with the respiratory waveform signal; and a display apparatus for inputting the facial image signal and the respiratory waveform signal synthesized and output from the synthesis section, chronologically continuously displaying the facial image with the area of the facial region of the facial image changing, and displaying a respiratory waveform so as to correspond to the facial image with the area of the facial region of the facial image changing.

A respiration monitor of the present invention is provided in that the predetermined imaging temperature range of the infrared camera is from 30 to 40° C., and the facial image is displayed in black and white in the respiration monitor.

A respiration monitor of the present invention is provided in that one portion of the facial region is defined and displayed as a black image corresponding to an inspiration and another portion of the facial region is defined and displayed as a white image corresponding to an expiration.

The present invention is provided in that: a face is imaged using an infrared camera while setting an imaging temperature within a predetermined temperature range and storing a facial image signal; the facial image signal is binarized to thereby define a facial region; and a respiratory waveform signal is found by calculating a change in an area of the facial region whose size changes so as to correspond to the inspired gas. When an apnea in which there is no change in the area of the facial region has been detected, an alarm signal is output to alarm the operator. Further, a respiratory waveform is synthesized so as to correspond to the facial region of the formed facial image whose size changes chronologically, and the synthesized respiratory waveform is continuously displayed on a screen of the display apparatus. As a result of this operation, respiratory conditions of the patient can be monitored in a non-contact manner, and when an apnea has been detected, an alarm is issued to inform the operator of the apnea. Therefore, respiratory conditions of the patient can be monitored in a non-contact manner, and when an apnea has been detected, an alarm is issued to inform the operator of the apnea, thereby allowing the operator to be informed of an emergency.

According to the present invention, the imaging temperature range of the infrared camera is set from 30° to 40° C. in the respiration monitor. Therefore, the facial image can be displayed in black and white.

The present invention is provided in that one portion of the facial region is defined and displayed as a black image corresponding to an inspiration, and another portion of the facial region is defined and displayed as a white image corresponding to an expiration in the respiration monitor.

DETAILED DESCRIPTION OF THE PREFERRED EMBODIMENTS

Figure 1:
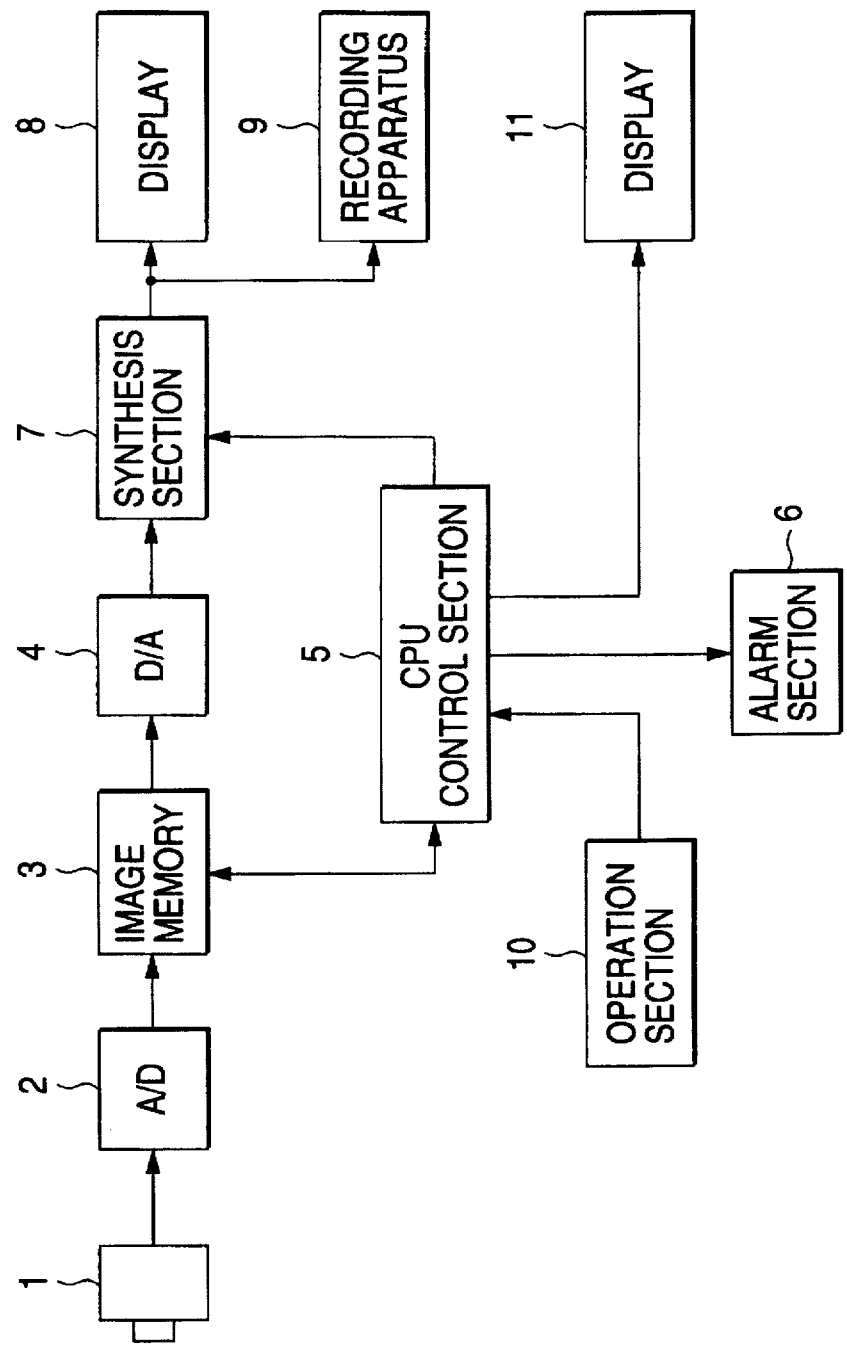
FIG. 1 is a block diagram showing a configuration of a respiration monitor, which is an embodiment of the invention.
Figure 2:
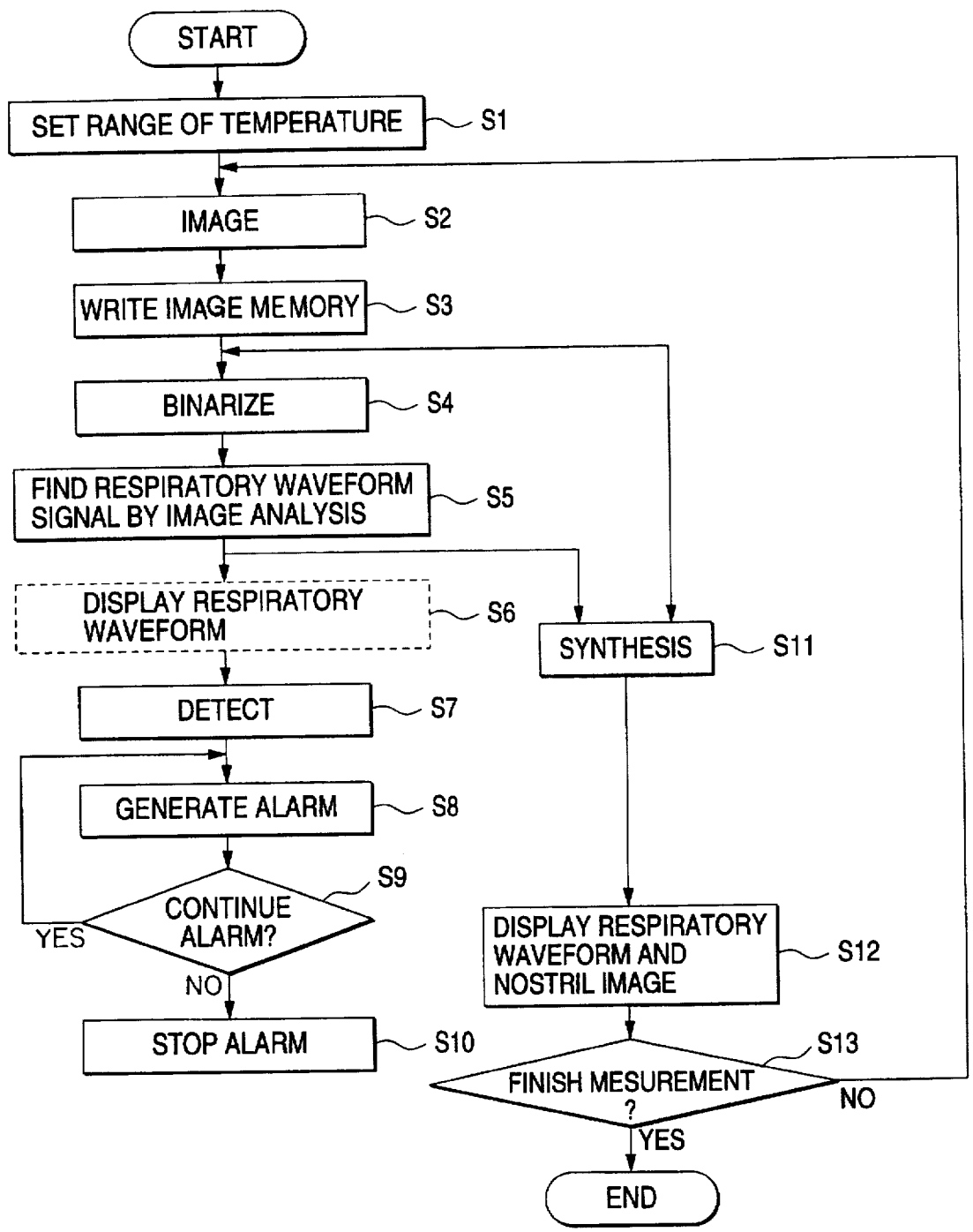
FIG. 2 is a flowchart showing a respiration detection flow in the embodiment shown in FIG. 1.
Figure 3:
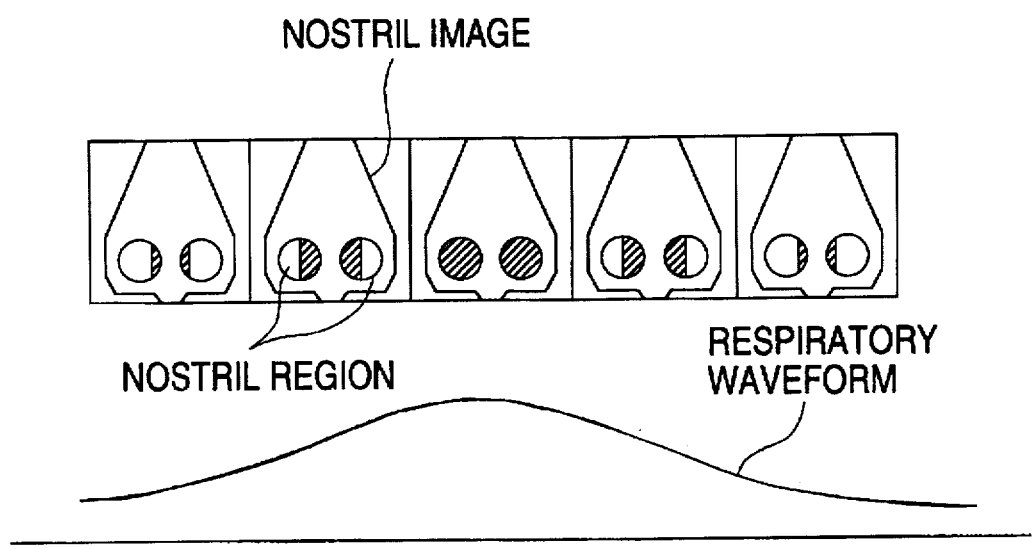
FIG. 3. is a diagram showing examples of a facial image and a respiratory waveform obtained by the embodiment shown in FIG. 1.

A respiration monitor, which is an embodiment of the invention, will now be described with reference to the drawings. FIG. 1 is a block diagram showing a configuration of a respiration monitor of the invention. FIG. 2 is a flowchart showing a respiration detection flow in the embodiment shown in FIG. 1. FIG. 3 is a diagram showing examples of a facial image and a respiratory waveform that change in accordance with respirations.

In FIG. 1, reference numeral 1 denotes, e.g., a small-sized infrared camera, which can be mounted on the frame of a bed or the like and held close to the nostrils of a patient who lies on the back on the bed, so that an image of the nostrils of the patient can be formed. The image of the nostrils is depicted in terms of a temperature change corresponding to the flow of the inspired gas during respiration, and when the image is displayed, the color of the image of the nostril region changes during respiration, inspiration, and apnea. That is, when the image of the nostrils is formed with the image forming temperature ranging from 30° to 40° C., the image of the nostrils of the patient can be obtained in black and white. The temperature range is set through an operation section that will be described later. The nostril region in the formed image is displayed in white since the temperature of the expired gas is higher than room temperature or ambient temperature during expiration and is displayed in black since the temperature of the inspired gas (air) is lower than the expired gas during inspiration. Further, when an apnea is detected, the nostril region is displayed in black during apnea in a manner similar to the case of expiration since there is no change in temperature brought about by the expired gas.

Reference numeral 2 denotes an analog-to-digital converter that converts an analog nostril image signal output from the infrared camera 1 into a digital nostril image signal; 3, an image memory constructed of, e.g., a video RAM that stores the digital nostril image signal input from the analog-to-digital converter 2; and 4, a digital-to-analog converter that converts the digital nostril image signal stored in the image memory 3 to an analog nostril image signal.

Reference numeral 5 denotes a control section constructed of, e.g., a CPU or the like including a RAM and a ROM. The ROM stores in advance a respiration program for detecting respirations. The control section 5 calculates the area of a region corresponding to the nostrils during respiration by binarizing the digital nostril image signal output from the image memory 3 and not only controls calculation of a respiratory waveform signal from the area but also supervises the apparatus in accordance with the respiration program. That is, the temperature of the nostril region fluctuates up and down in response to the expired and inspired gases, and this temperature fluctuation increases and decreases the black region. It is the area of this black region that is calculated by the control section 5. On the other hand, there is no temperature fluctuation during apnea, so that there is no change in area in the black and white image. When the apnea has been detected from a differentiated value (slope) of the waveform indicating that such area of the black region is 0, the control section 5 outputs an alarm signal. Further, the respiratory waveform signal can be found by calculating the area of the nostril region in the nostril image displayed in black during inspiration.

Reference numeral 6 denotes an alarm section, which is constructed of, e.g., a light-emitting diode (LED) or the like and issues an alarm by, e.g., lighting or blinking in response to an alarm signal output from the control section 5. Further, the alarm section 6 can be designed so that an alarm sound can be generated by using, e.g., a buzzer or a small-sized loudspeaker. An optical alarm and a sound alarm may be generated at the same time by combining an LED and a buzzer or small-sized loudspeaker together.

Reference numeral 7 denotes a synthesis section that synthesizes the analog nostril image signal sent from the digital-to-analog converter 4 with the respiratory waveform signal converted into an analog signal by a digital-to-analog converter (not shown) incorporated in the control section 5, and outputs the synthesized signal.

Reference numeral 8 denotes a display apparatus constructed of, e.g., a liquid crystal display or a CRT. The display apparatus 8 displays both the analog nostril image signal and the respiratory waveform signal output from the synthesis section 7 on a screen thereof. Reference numeral 9 denotes a recording apparatus, which receives both the analog nostril image signal and the respiratory waveform signal output from the synthesis section 7 and records the nostril image and respiratory waveform on a recording sheet.

Further, reference numeral 10 denotes the operation section constructed of, e.g., a keyboard. The operation section 10 performs the functions of setting the temperature range of the infrared camera 1, setting various data, and activating and stopping the apparatus, etc. Still further, reference numeral 11 denotes a display apparatus that is similar to the display apparatus 8 and that displays only respiratory waveforms output from the control section 5. It may be noted that the display apparatus 11 can be omitted since this display apparatus has the function of displaying merely respiratory waveforms. If the display apparatus 11 is omitted, it may be so arranged that the recording apparatus 9 records respiratory waveforms.

Then, an operation of the thus constructed respiration monitor will be described with reference not only to a flowchart shown in FIG. 2 but also to display examples of a nostril image and a respiratory waveform shown in FIG. 3.

The operator sets from the operation section 10 the temperature range to, e.g., 32° to 36° C. within the range of from 30° to 40° C., taking ambient temperature or the temperature of a patient into consideration (Step S1). When the temperature range setting operation has been ended, the nostrils of the patient are imaged by the infrared camera 1 (Step S2), and a digital nostril image signal is written into the image memory 3 through the analog-to-digital converter 2 (Step S3). The control section 5 receives the digital nostril image signal from the image memory 3 and binarizes the received signal in order to calculate the area of the nostril region (Step S4).

Based on the digital nostril image signal binarized in Step S4, the control section 5 defines the nostril region, and calculates the areas of a black region and a white region in the nostril region, whose sizes change as the patient breathes through his or her nostrils, and finds a respiratory waveform signal (Step S5), and converts the respiratory waveform signal into an analog signal and outputs the analog signal. The respiratory waveform signal is sent to the display in apparatus 11, which displays the respiratory waveform (Step S6). If the display apparatus 11 is not arranged, Step S6 is skipped and Step S7 is performed from Step S5.

Upon detection of absence of a change in the nostril region of the black and white image indicating the respiration by monitoring the respiratory waveform signal (Step S7), the control section 5 delivers an alarm signal to the alarm section 6 and causes the alarm section 6 to generate an alarm by, e.g., blinking (Step S8). The operator judges whether or not the alarm should be continued (Step S9), and if it is judged to stop alarming, the alarm is reset (Step S10) by operating, e.g., an alarm reset key (not shown) of the control section 10, and if it is judged to continue alarming, Step S8 is performed.

On the other hand, the digital nostril image signal stored in the image memory 3 in Step S4 is converted into an analog nostril image signal by the digital-to-analog converter 4, and the converted analog nostril image signal is synthesized with the respiratory waveform signal calculated by the control section 5 in Step S5 at the synthesis section 7 (Step S11).

The signal having both the respiratory waveform signal and the nostril image signal synthesized at the synthesis section 7 is output to the display apparatus 8, and a respiratory waveform and a nostril image in which the area of the nostril region chronologically changes are displayed so as to correspond to each other (Step S12). That is, the nostril region is displayed in white during expiration, whereas the black area of the nostril region is displayed so as to increase or decrease in accordance with the inspired gas during inspiration. Therefore, when the patient suffers from an apnea, the black and white areas in the nostril region on the screen of the display apparatus 8 exhibits no change. Therefore, if, e.g., an interval in which there is no change in area lasts for 20 seconds or more, it is judged that the patient is in apnea. Hence, even if a respiratory waveform obtained from a respiratory sensor that is concurrently measuring respirations by means of, e.g., the impedance method or the like is not reliable due to the respiratory sensor operating erroneously, the apnea can be judged at a glance from the nostril image, which in turn allows the operator to give the patient an emergency treatment.

If the measurement is no longer continued, the operation is terminated, and if the measurement is to be continued, the imaging operation in Step S2 is performed again and the operations in step S2 et seq. are repeated (Step S13).

As described above, the invention is provided as forming an image of the nostrils using an infrared camera, displaying a change in area corresponding to a respiration in the nostril region of a nostril image in the form of a black and white image, and generating an alarm upon detection of an apnea. Therefore, respiratory conditions of a patient can be monitored in a noncontact and noninvasive manner with ease.

While attention has been given to temperature change brought about by respirations through the nostrils in this embodiment, respiratory conditions can be monitored similarly by giving attention to temperature change brought about by respirations through the mouth.

As described in the foregoing, the respiratory monitor provides imaging respiratory conditions of a patient using an infrared camera and displaying a facial image so as to correspond to a respiratory waveform. Therefore, the invention can provide the advantage that respiratory conditions can be monitored in a non-contact manner and that the cumbersome operation of handling the lead wires can be eliminated with no electrodes or sensors attached to the body to ensure non-invasiveness. Moreover, upon detection of an apneic condition, an alarm is generated, which in turn allows the respiratory conditions of the patient to be monitored stably and contributes to providing the patient with a swift treatment during the apnea.

According to the present invention, the facial image is displayed in black and white. Therefore, the invention as recited in claim 2 can provide the advantage that an image of expiration is sharply contrasted to an image of inspiration in the facial region, which in turn facilitates reliable judgment of respiratory conditions.

According to the present invention the facial region during expiration is displayed in white and the facial region during inspiration is displayed in black so that there is no change in the white and black portions of the facial region during apnea. Therefore, the apnea can be recognized at a glance.

What is claimed is:

1. A respiration monitor comprising:
   an infrared camera for forming an image of a face;
   an operation section for selecting an imaging temperature to be set for said infrared camera, from a predetermined temperature range, and setting a selected imaging temperature;
   an image memory for storing a facial image signal output from said infrared camera;
   a control section for defining a facial region in said facial image signal, binarizing said facial image signal within said facial region, calculating and outputting a respiratory waveform signal from a change in an area of said facial region every respiration, and outputting an alarm signal upon detection of an apnea when a condition in which there is no change in the area of said facial region for a predetermined time;
   an alarm section for generating an alarm in response to said alarm signal;
   a synthesis section for synthesizing said facial image signal with said respiratory waveform signal; and
   a display apparatus for receiving said facial image signal and said respiratory waveform signal synthesized and output from said synthesis section, chronologically and continuously displaying said facial image with the area of said facial region of said facial image changing, and displaying a respiratory waveform so as to correspond to said facial image with the area of said facial region of said facial image changing.

2. A respiration monitor according to claim 1, wherein said predetermined temperature range of said infrared camera is from 30° to 40° C., and said facial image is displayed in black and white.

3. A respiration monitor according to claim 1, wherein one portion of said facial region is defined and displayed as a black image corresponding to an inspiration and another portion of said facial region is defined and displayed as a white image corresponding to an expiration.

4. A method for monitoring a respiration comprising the steps of:
   forming an image of a face by an infrared camera;
   storing a facial image signal output from said infrared camera;
   defining a facial region in said facial image signal;
   binarizing said facial image signal within said facial region;
   calculating and outputting a respiratory waveform signal from a change in an area of said facial region every respiration;
   outputting an alarm signal by judging an apnea when a condition in which there is no change in the area of said facial region for a predetermined time;
   generating an alarm in response to said alarm signal;
   synthesizing said facial image signal with said respiratory waveform signal;
   inputting to a display said facial image signal and said respiratory waveform signal synthesized and output from said synthesis section;
   chronologically and continuously displaying said facial image with the area of said facial region of said facial image changing; and
   displaying a respiratory waveform so as to correspond to said facial image with the area of said facial region of said facial image changing.

5. A method for monitoring a respiration as claimed in claim 4, further comprising the steps of:
   selecting an image temperature to be set for said infrared camera, from a predetermined temperature range, and setting a selected imaging temperature.

* * * * *